United States Patent [19]

Pelosi, Jr. et al.

[11] 4,403,097

[45] Sep. 6, 1983

[54] 5-(3-TRIFLUOROMETHYLPHENYL)-2-FURANCARBOXYLIC ACID 2-(1-METHYLETHYLIDENE)HYDRAZIDE

[75] Inventors: Stanford S. Pelosi, Jr.; Chia-Nien Yu, both of Norwich, N.Y.

[73] Assignee: Norwich Eaton Pharmaceuticals, Inc., Norwich, N.Y.

[21] Appl. No.: 384,870

[22] Filed: Jun. 4, 1982

[51] Int. Cl.$^3$ .......................................... C07D 307/68
[52] U.S. Cl. ................................................. 549/487
[58] Field of Search ....................................... 549/487

[56] References Cited

PUBLICATIONS

Oleinik et al., Chem. Abstracts 6162p (1978).

Primary Examiner—Alan L. Rotman
Assistant Examiner—Bernard Dentz
Attorney, Agent, or Firm—Anthony J. Franze

[57] ABSTRACT 5-(3-Trifluoromethylphenyl)-2-furancarboxylic acid 2-(1-methylethylidene)hydrazide is an effective skeletal muscle relaxant.

1 Claim, No Drawings

5-(3-TRIFLUOROMETHYLPHENYL)-2-FURANCARBOXYLIC ACID 2-(1-METHYLETHYLIDENE)HYDRAZIDE

This invention relates to the compound 5-(3-trifluoromethylphenyl)-2-furancarboxylic acid 2-(1-methylethylidene)hydrazide of the formula:

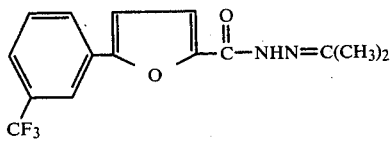

This compound possesses pharmacologic activity. In particular it exhibits skeletal muscle relaxant activity when administered perorally to warm-blooded animals. Thus, when administered perorally as a suspension in a pharmaceutically acceptable vehicle, such as aqueous methyl cellulose, at a dose of 400 mg/kg to mice, skeletal muscle relaxant activity is elicited.

The compound of this invention is readily prepared by reacting 5-(3-trifluoromethylphenyl)-2-furancarboxylic acid hydrazide with acetone. In order that this invention may be readily available to and understood by those skilled in the art, the method now preferred for making it is described:

A solution of 38 g (0.135 mole) of 5-(3-trifluoromethylphenyl)-2-furancarboxylic acid hydrazide and 400 ml of acetone was refluxed overnight. The solvent was removed on the Calab evaporator and the residual solid was washed with hexane and dried at 60° to yield 37 g (88%) of product. An analytical sample was prepared by recrystallizing a sample from ethyl acetate (Darco) and drying 48 hrs in the vacuum pistol at the temperature of boiling water, m.p. 120°–122°.

Anal. Calcd. for $C_{15}H_{13}F_3N_2O_2$: C, 58.06; H, 4.22; N, 9.03; Found: C, 58.07; H, 4.39; N, 9.11.

What is claimed is:

1. The compound 5-(3-trifluoromethylphenyl)-2-furancarboxylic acid 2-(1-methylethylidene)hydrazide.

* * * * *